United States Patent [19]

Civilla et al.

[11] Patent Number: 4,541,860

[45] Date of Patent: Sep. 17, 1985

[54] STABLE COMPOSITIONS OF N-(3,4-DICHLOROPHENYL)-N'-METHOXY-N'-METHYLUREA (LINURON) AND 2,6-DINITRO-N,N-DIPROPYL-4-TRI-FLUORO-METHYLANILINE (TRIFLURALIN) IN EMULSION

[75] Inventors: Enzo Civilla, Milan; Piero Furlan, Peschiera Borromeo; Sergio Maccone, Milan, all of Italy

[73] Assignee: Montedison S.p.A., Milan, Italy

[21] Appl. No.: 534,764

[22] Filed: Sep. 22, 1983

Related U.S. Application Data

[63] Continuation of Ser. No. 270,804, Jun. 5, 1981, abandoned.

[30] Foreign Application Priority Data

Jun. 6, 1980 [IT] Italy .................... 22622 A/80

[51] Int. Cl.$^4$ .................................. A01N 25/22

[52] U.S. Cl. ......................... 71/120; 71/121; 71/DIG. 1

[58] Field of Search ................ 71/DIG. 1, 120, 121

[56] References Cited

U.S. PATENT DOCUMENTS

| 4,163,662 | 8/1979 | Baker, Jr. ............... | 71/120 |
| 4,213,776 | 7/1980 | Giilck et al. ............ | 71/117 |
| 4,283,222 | 8/1981 | Horide et al. ........... | 71/120 |

FOREIGN PATENT DOCUMENTS 2037265  2/1972  Fed. Rep. of Germany .
2239941  8/1983  France .

Primary Examiner—Catherine L. Mills

[57] ABSTRACT

Stable herbicidal compositions, more particularly stable emulsions, based on N-(3,4-dichlorophenyl)-N'-methoxy-N'-methylurea ("Linuron") and 2,6-dinitro-N,N-dipropyl-4-trifluoromethylaniline ("Trifluralin") are disclosed.

4 Claims, No Drawings

STABLE COMPOSITIONS OF N-(3,4-DICHLOROPHENYL)-N'-METHOXY-N'-METHYLUREA (LINURON) AND 2,6-DINITRO-N,N-DIPROPYL-4-TRIFLUORO-METHYLANILINE (TRIFLURALIN) IN EMULSION

This is a continuation of application Ser. No. 270,804, filed June 5, 1981, now abandoned.

BACKGROUND OF THE INVENTION

Linuron and Trifluralin are two weed-killers known in the literature. Their association permits control of a great number of infesting plants in agrarian cultures.

According to German patent application No. 2,037,265 the above-mentioned weed-killers can be simply mixed in a mixer before being used. Of course, they can be also individually spread on the soil.

This is inconvenient in practice, as it involves expensive treatments and handlings and can lead to errors of dosage.

Consequently, the procedure generally followed consists in spreading on the soil previously prepared compositions which, beside ensuring a correct dosage, do not require any particular treatments before being used.

As is known, the compositions most suitable for being spread on the soil are aqueous emulsions, which offer the advantage that they can be distributed uniformly by atomization and spraying by means of proper pumps, do not involve fatigue and are correctly vehicled to reach the infesting plants.

Unfortunately Linuron is insoluble in the common solvents which are not phytotoxic and often the emulsions prepared therefrom are not stable.

According to French patent application No. 2,239,941, Trifluralin and Linuron can be dissolved, in ratios of from 4:1 to 1:4, preferably from 2:1 to 1:2, in an alicyclic non-phytotoxic ketone, such as, for example, the cycloalkyl- or cycloalkenyl-ketones, in particular cyclohexanone or substituted cyclohexanones, in an amount sufficient to dissolve the weed-killers; the resulting solution can be then diluted with other solvents mixable with the alicyclic ketone; or furthermore, the mixture of weed-killers can be dissolved in a mix of an alicyclic ketone and a solvent mixable with said ketone, the latter being in an amount sufficient to dissolve the herbicides.

Aqueous emulsions can be prepared from such solutions already additioned with suitable anionic and non-ionic emulsifiers.

It is a common practice to sell the solutions as described hereinabove and to mix them with water at the time of use.

It has been observed that the aqueous emulsions prepared by using the compositions described in German patent application No. 2,037,265 at the concentrations employed for agricultural weed killing (from 0.375 to 1.5% in water) quickly deposit crystals of solid herbicides, which tend to settle on the bottom of the containers in which the emulsion is prepared, so subtracting active principle from the weed killer and often clogging the distributing pumps.

THE PRESENT INVENTION

An object of this invention is to provide solutions of Linuron and Trifluralin which are emulsificable with water and which, once emulsified, result in aqueous emulsions which remain stable over long periods of time without depositing crystals.

This and other objects are achieved by the present invention in accordance with which there are provided solutions of Trifluralin, Linuron and acetophenone additioned with the usual emulsifiers and the solvents mixable with acetophenone, and which once they have been emulsified in water, do not give rise to the crystal deposition phenomenon.

The amounts of the various components can be comprised within the following limits:

|  | % by weight |
| --- | --- |
| Trifluralin | 20.0–36.0 |
| Linuron | 5.0–12.4 |
| Acetophenone | 17.0–36.1 |
| Emulsifiers | 5.0–10.5 |
| Xylene or another aromatic solvent mixable with acetophenone | 53.0–5.0 |

Under these conditions, crystals do not form even after 17 hours from the preparation of the emulsion, as is proved in the examples infra.

Trifluralin and Linuron employable according to the present invention do not require any particular purification treatments, and it is possible to use the technical-grade products having a purity of 95%.

The solvents mixable with acetophenone are the aromatic solvents, such as the xylenes; or the aromatic-aliphatic solvents such as "Shellsol" or "Solvesso" (mixtures of alkylbenzenes). We have found that the mixture of xylenes, generally referred to as xylene or xylol, is particularly suitable for the purposes to be achieved.

It is also desirable to use more than one emulsifier: a mixture of emulsifiers consisting for 30% of calcium alkylbenzenesulphate and for 60% of alkylphenyl condensed with ethylene oxide and propylene oxide and for 10% of bis-α-ethylphenylphenol-polyoxyethylate has proved particularly effective.

The solutions of this invention, at concentrations of 0.375 to 1.5% in water, provide, after emulsification, emulsions which, after 17 hours, do not exhibit any traces of crystalline precipitate.

EXAMPLES A to E

The following solutions were prepared, C and D being comparative:

|  |  | % by weight |
| --- | --- | --- |
| (A) | Trifluralin (1) | 24.8 |
|  | Linuron (1) | 5.0 |
|  | Acetophenone | 17.0 |
|  | Mixture of emulsifiers (2) | 5.0 |
|  | Xylene | 48.2 |
| (B) | Trifluralin (1) | 36.0 |
|  | Linuron (1) | 12.4 |
|  | Acetophenone | 36.1 |
|  | Mixture of emulsifiers (2) | 10.0 |
|  | Xylene | 5.5 |
| (C) | Trifluralin (1) | 24.8 |
|  | Linuron (1) | 5.0 |
|  | Cyclohexanone | 17.0 |
|  | Mixture of emulsifiers (2) | 5.0 |
|  | Xylene | 48.2 |
| (D) | Trifluralin (1) | 36.0 |
|  | Linuron (1) | 12.4 |
|  | Cyclohexanone | 36.1 |
|  | Mixture of emulsifiers (2) | 10.0 |
|  | Xylene | 25.5 |

|   | % by weight |
|---|---|
| (E) Trifluralin (1) | 21.0 |
| Linuron (1) | 5.0 |
| Acetophenone | 17.0 |
| Mixture of emulsifiers (2) | 5.0 |
| Xylene | 52.0 |

(1) Trifluralin technical grade having a purity of 95%; Linuron technical grade having a purity of 95%.
(2) Mixture consisting for 30% of calcium alkylbenzene-sulphonate and for 70% of alkylphenol condensed with ethylene oxide and propylene oxide.

The necessary amount of standard hard water (342 ppm expressed as calcium carbonate) was introduced, at 30° C., into 8 graduated cylinders having a capacity of 100 cc each and provided with frosted plugs, each cylinder having been filled up to 100 cc as follows:

4 cylinders with 0.375 cc of solutions A, B, C, D, E
4 cylinders with 1.5 cc of solutions A, B, C, D, E.

The cylinders were closed and continuously turned upside down 30 times in 60 seconds, whereupon the plugs were removed and the cylinders were left in a bath at 30° C. for 8 hours.

At the conclusion of said period, in all of the four cylinders containing comparative emulsions C and D it was possible to observe a needle-like precipitate, while the cylinders containing emulsions A, B and E of this invention were free therefrom.

The latter cylinders, after reading, were placed again into the bath at 30° C. and were allowed to stand there for 17 hours. At the end of that time-period, no crystalline precipitate was observed.

What we claim is:

1. A weed-killing composition which is emulsifiable in water, does not give rise to crystalline precipitates for at least 17 hours after emulsification, and consists of:

|   | % by weight |
|---|---|
| 2,6-dinitro-N,N—dipropyl-4-trifluoromethylaniline | 20.0–36.0 |
| N—(3,4-dichlorophenyl)-N'—methoxy-N'—methylurea | 5.0—12.4 |
| acetophenone | 17.0–36.1 |
| emulsifiers | 5.0–10.5 |
| xlylene or mixed alkylbenzenes mixable with acetophenone | 53.0–5.0 |

2. A composition according to claim 1, characterized in that the emulsifiers are a mixture of 30% calcium alkylbenzenesulphonate and of 70% alkylphenol condensed with ethylene oxide and propylene oxide.

3. A composition according to claim 1, consisting of:

|   | % by weight |
|---|---|
| 2,6-dinitro-N,N—dipropyl-4-trifluoromethylaniline | 24.8 |
| N—(3,4-dichlorophenyl)-N'—methoxy-N'—methylurea | 12.4 |
| acetophenone | 36.1 |
| Mixture of 30% calcium alkylbenzenesulphonate and 70% alkylphenol condensed with ethylene oxide and propylene oxide | 10.0 |
| xylene | 16.7 |

4. A stable emulsion resulting from emulsification of the composition of claim 1.

* * * * *